(12) United States Patent
Beisser et al.

(10) Patent No.: US 11,484,696 B2
(45) Date of Patent: Nov. 1, 2022

(54) CLAMP

(71) Applicant: FRESENIUS MEDICAL CARE DEUTSCHLAND GMBH, Bad Homburg (DE)

(72) Inventors: Nicolas Beisser, Hanau (DE); Arne Peters, Bad Homburg (DE); Alexander Heide, Eppstein (DE); Gerome Fischer, Weberstedt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 273 days.

(21) Appl. No.: 16/754,145

(22) PCT Filed: Oct. 12, 2018

(86) PCT No.: PCT/EP2018/077813
§ 371 (c)(1),
(2) Date: Apr. 7, 2020

(87) PCT Pub. No.: WO2019/073016
PCT Pub. Date: Apr. 18, 2019

(65) Prior Publication Data
US 2020/0330742 A1 Oct. 22, 2020

(30) Foreign Application Priority Data

Oct. 12, 2017 (DE) .................. 10 2017 218 216.4
Sep. 4, 2018 (DE) .................. 10 2018 214 989.5

(51) Int. Cl.
*A61M 39/28* (2006.01)
*F16K 7/04* (2006.01)

(52) U.S. Cl.
CPC ............. *A61M 39/28* (2013.01); *F16K 7/045* (2013.01); *A61M 2205/0272* (2013.01)

(58) Field of Classification Search
CPC ........ F16K 7/061; F16K 7/045; A61M 39/28; A61M 39/284; A61M 39/283; A61M 2205/0272; A61M 2205/8287
See application file for complete search history.

(56) References Cited

U.S. PATENT DOCUMENTS

| 3,511,469 A | * | 5/1970 | Bell | ........................ F16K 7/045 251/285 |
| 3,985,722 A | * | 10/1976 | Yoshida | ................ C07C 233/45 530/820 |

(Continued)

FOREIGN PATENT DOCUMENTS

| EP | 1132108 A1 | 9/2001 |
| JP | 5639370 A | 4/1981 |

(Continued)

OTHER PUBLICATIONS

International Preliminary Report on Patentability issued in corresponding International Patent Application No. PCT/EP2018/077813 (English translation) dated Apr. 14, 2020 (9 pages).

(Continued)

*Primary Examiner* — Kelsey E Cary
(74) *Attorney, Agent, or Firm* — Kilyk & Bowersox, P.L.L.C.

(57) ABSTRACT

The invention relates to a clamp (1), which is such that the clamp (1) can accommodate a fluid-carrying duct (L), that the clamp (1) in a resting state can compress the accommodated fluid-carrying channel (L), and that in a working state the clamp (1) can accommodate the fluid-carrying channel (L) so that the fluid-carrying channel (L) is not compressed, wherein the clamp (1) has a first permanent magnet (M1) and a second permanent magnet (M2), the permanent magnets (M1, M2) being arranged at a distance from one another, such that the permanent magnets (M1, M2) can be rotated at least about an angle relative to one another, the (Continued)

relative rotation of the permanent magnets (M1, M2) to one another resulting in a reduction in the distance (d), the resting state being made available at a first angle and the working state being made available at a second angle.

13 Claims, 6 Drawing Sheets

(56) References Cited

U.S. PATENT DOCUMENTS

| 2001/0019117 | A1* | 9/2001 | Schoeb | F16K 7/045 |
| | | | | 251/65 |
| 2014/0318639 | A1 | 10/2014 | Peret et al. | |
| 2019/0234524 | A1* | 8/2019 | Attili | F16K 31/0651 |

FOREIGN PATENT DOCUMENTS

| WO | 2005117240 A2 | 12/2005 |
| WO | 2011121923 A1 | 10/2011 |

OTHER PUBLICATIONS

International Search Report and Written Opinion issued in corresponding International Patent Application No. PCT/EP2018/077813 (with English translation of International Search Report) dated Jan. 21, 2019 (16 pages).

* cited by examiner

CLAMP

This application is a National Stage Application of PCT/EP2018/077813, filed Oct. 12, 2018, which claims priority to German Patent Application No. 10 2018 214 989.5, filed Sep. 4, 2018 and German Patent Application No. 10 2017 218 216.4, filed Oct. 12, 2017.

BACKGROUND

Clamps are used in many fields of medical technology to make it possible to switch the flow through a fluid-carrying channel, such as a tubing line, for example, or a channel, which is enclosed in a cassette and bordered by a flexible wall.

Such switchable clamps have a clamp element, a spring element and a current-controlled holding element. The spring element supplies a closing force to block the clamp in the currentless state of the holding element. In this state, the clamp element in a closed position blocks the fluid-carrying channel, and a fluid distribution line is suppressed.

In this case, the fluid may be a liquid or a gas.

In the event of a power outage, for example, the blocking position in a currentless state is advantageous in particular because a further (uncontrolled) supply of substances to a human or animal body should be suppressed.

When the clamps are in an open position, an electric current acts on a holding element, for example, an electromagnetic. The holding element thus supplies a holding force, which counteracts the spring force and holds the clamping element in the open position.

Figure 6:
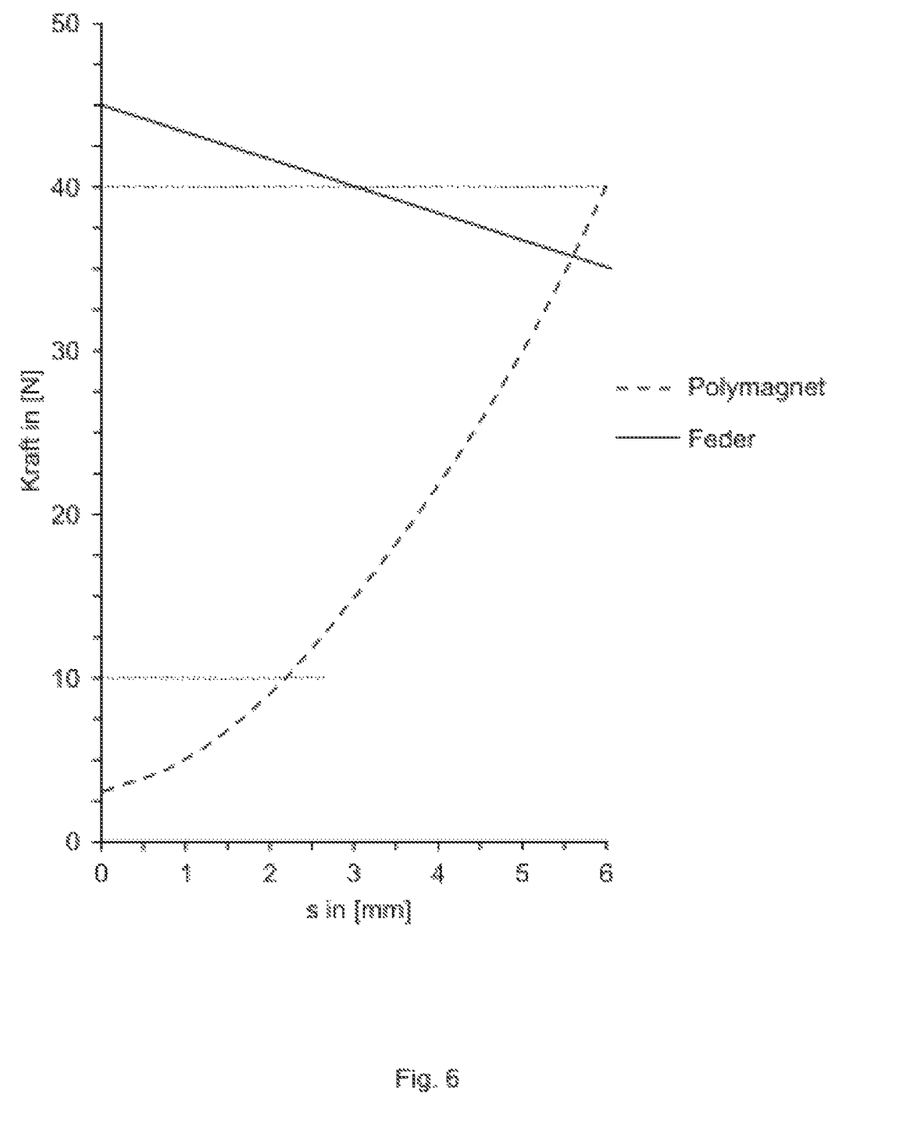
FIG. 6 shows a force-distance diagram of screw clamps from the state of the art as well as according to specific embodiments of the invention.
Figure 7:
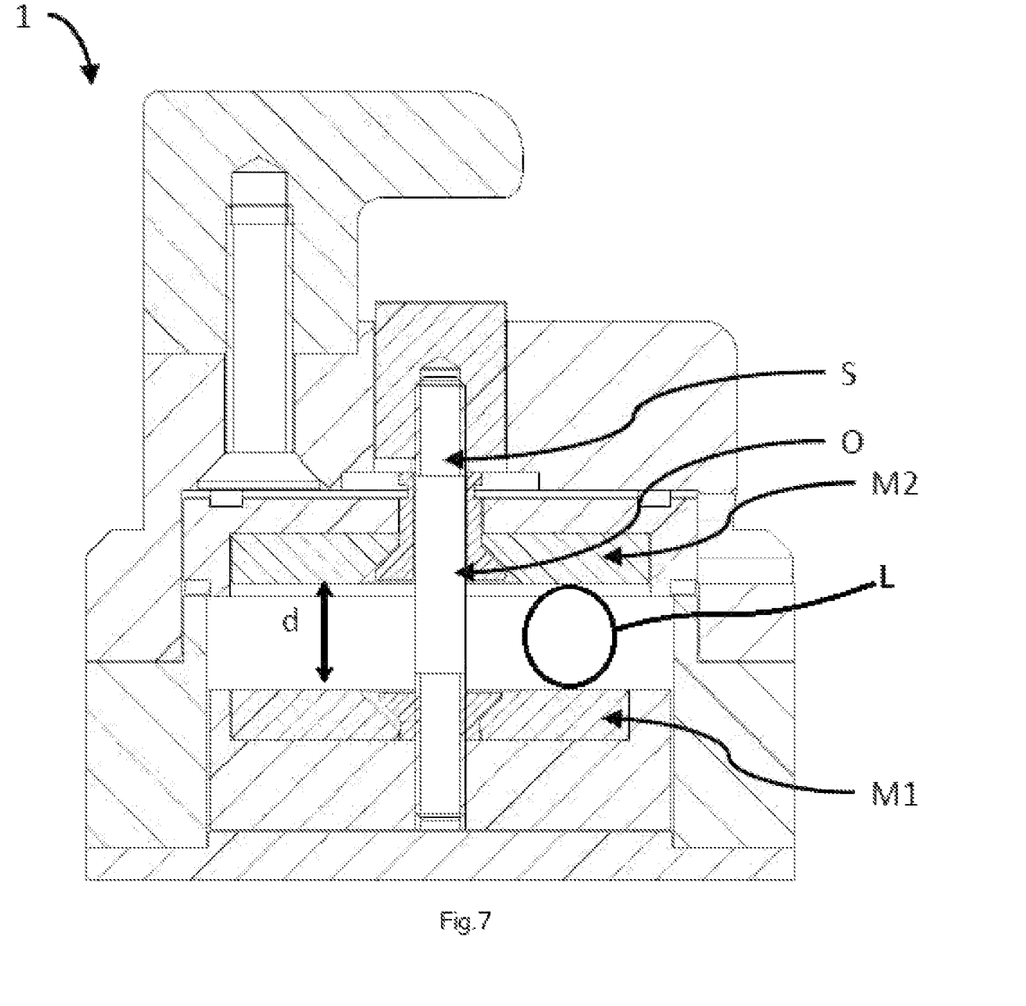
FIG. 7 shows an example of a sectional diagram of elements of a clamp according to another embodiment of the present invention, wherein the fluid-carrying channel (L) is arranged between the first permanent magnet M1 and the second permanent magnet M2.

One disadvantage of this arrangement is that, because of the linear force-distance characteristic, the holding force must be fundamentally higher than the closing force provided by the spring element (see FIG. 6).

In addition, a higher closing force requires a higher holding force accordingly.

A higher closing force requires a spring element having larger dimensions and therefore a greater weight and therefore also a heavy electromagnet, higher holding currents, higher energy consumption.

On one hand, this increases the cost of manufacturing and, on the other hand, also increases operating costs.

OBJECT

One object of the invention is therefore to provide a clamp that can be manufactured less expensively and has lower operating costs. It is a further object of the invention to provide clamps, the operation of which requires significantly less energy as compared to known clamps.

BRIEF DESCRIPTION OF THE INVENTION

This object is achieved by a clamp, which is such that the clamp can accommodate a fluid-carrying channel, that the clamp can compress the fluid carrying channel in a resting state and that in a working state the clamp can accommodate the fluid-carrying duct such that the fluid-carrying duct is not compressed, wherein the clamp has a first permanent magnet and a second permanent magnet, the permanent magnets being arranged at a distance from one another so that the permanent magnets can be rotated at least by an angle relative to one another, the relative rotation of the permanent magnets to one another resulting in a reduction in the distance, the resting state being provided at a first angle, and the working state being provided at a second angle.

The permanent magnets can in particular be arranged so as to be moveable relative to one another, wherein the permanent magnets can be rotated at least by an angle relative to one another, and wherein the permanent magnets can be moved linearly relative to one another, so that the distance between the permanent magnets can vary, wherein a rotation of the permanent magnets relative to one another leads to a change of the relative arrangement of the poles of the permanent magnets to one another, which, in turn, effects a change of the magnetic attractions between the magnets, as a result of which a change of the distance of the permanent magnets takes place, wherein the clamp in a first relative rotational position of the permanent magnets to one another assumes a resting state, and in a second relative rotational position of the permanent magnets to one another assumes a working state.

A fluid-carrying channel may be, for example, a tubing line or a channel created in a cassette and delimited by a flexible wall.

It is possible by means of the invention to provide a clamp, which permits a simple mechanical design with reduced holding currents at the same time.

In the case of one embodiment of a clamp (1) proposed here, the clamp (1) blocks flow by compression of a fluid-carrying channel (L) in a resting state and enables flow in a working state by releasing the compression. The clamp (1) thereby has a first magnet (M1) and a second magnet (M2), wherein the magnets (M1, M2) are arranged at a distance from one another so that the magnets (M1, M2) can be rotated at least by an angle relative to one another, the relative rotation of the magnets (M1, M2) to one another resulting in a reduction in the distance (d), the resting state being provided at a first angle, and the working state being provided at a second angle.

In one specific embodiment of the invention, the fluid is a liquid, i.e., the invention allows control of the supply of dialysate or other substances, for example.

In another specific embodiment of the invention, a fluid-carrying (inserted) channel is arranged between the permanent magnets.

According to another specific embodiment of the invention, the first permanent magnet and/or the second permanent magnet is/are a so-called polymagnetized magnet, such a magnet having a first number of sectors of a first magnetization and a second number of sectors of a second opposing magnetization.

Elements that are rotatable and/or displaceable relative to one another can be implemented especially easily in a small space by means of polymagnetized magnets.

In another specific embodiment of the invention, the difference in amount between the first angle and the second angle is less than or equal to 360° divided by the number of sectors, i.e., the required forces can be applied even with a rotation of less than 180°.

In yet another specific embodiment of the invention, a lever is also provided for opening the clamp, so that a fluid-carrying channel can be inserted into the clamp.

The clamp can also be opened by the lever in a currentless state, so that a fluid-carrying channel can be inserted.

According to another specific embodiment of the invention, an electromagnet is also provided, acting on at least one of the permanent magnets in the case of activation so that the working state is maintained, i.e., the electromagnet is designed so that the continuous flow through the fluid-carrying channel is made possible.

According to a refinement of the invention, the electromagnet acts on at least one of the permanent magnets in the case of activation, so that the working state is reached, i.e., the electromagnet is designed so that it is possible to switch from the resting state to the working state.

This specific embodiment is suitable in particular with clamps for channels, through which medical fluids, such as blood or infusion fluids are passed into or out of a patient. The clamp may be designed as part of a blood treatment machine, a peritoneal dialysis machine or an infusion pump, for example. If fault situations occur with such machines, in particular in the event of an interruption in the electrical power supply to the machine, it is necessary in general to induce a safe condition, in which the fluid connection to the patient is interrupted. A holding element designed as an electromagnet, which switches from the resting state to the working state by activation by means of power consumption, would necessarily switch from the working state to the resting state in the event of a power failure and would interrupt the flow through the channel.

According to one refinement of the invention, the first permanent magnet is guided relative to the second permanent magnet on a helical path in the transition from the resting state to the working state.

Different path profiles can thus be made available in this way.

In another specific embodiment, a rod-type shape of the closing force is available, wherein the force characteristic of the magnet pair, which is formed by the first permanent magnet and the second permanent magnet, is implemented, wherein the attractive force is great when the distance between the permanent magnets is small, is converted into a force characteristic of the closing force, which is great when the clamp is closed.

Additional advantageous embodiments are the subject matter of the dependent claims and the detailed description.

BRIEF DESCRIPTION OF THE FIGURES

The invention is explained in greater detail below with reference to the figures, in which.

DETAILED DESCRIPTION

The invention is described in greater detail below with reference to the figures. It should be pointed out here that various aspects, which may be used individually or in any combination, are described, i.e., each aspect may be used with different specific embodiments of the invention unless explicitly identified as a strict alternative.

Furthermore, for the sake of simplicity, reference is always made below to only one entity. Unless pointed out explicitly, however, the invention may also comprise a plurality of entities thus affected. To this extent, the use of the words "a," "an" and "one" are to be understood only as a reference to the fact that at least one entity is used in a simple specific embodiment.

A clamp 1 is made available according to the invention.

In a resting state, the clamp 1 blocks the through-flow by compressing an inserted fluid-carrying channel L. In a working state of the clamp 1, however, the flow through the inserted fluid-carrying channel L is enabled by reversing the compression.

This means that the clamp 1 can be such that the clamp 1 can accommodate a fluid-carrying channel L, wherein in a resting state the clamp 1 can compress the accommodated fluid-carrying channel L and that in a working state the clamp 1 can accommodate a fluid-carrying channel so that it is not compressed.

To this end, the clamp 1 has a first magnet, i.e. a permanent magnet, M1 and a second magnet, i.e. a permanent magnet, M2, the magnets M1, M2 being arranged at a distance from one another so that the magnets M1, M2 can be rotated by at least an angle relative to one another, wherein the rotation of the magnets M1, M2 relative to one another results in a reduction in the distance d, wherein the resting state is made available at a first angle and the working state is made available at a second angle.

In one embodiment, the permanent magnets M1, M2 can in particular also be arranged so as to be moveable relative to one another so that the permanent magnets M1, M2 can be rotated at least by an angle relative to one another, and that the permanent magnets M1, M2 can be moved linearly relative to one another, so that the distance d between the permanent magnets M1, M2 can vary, wherein a rotation of the permanent magnets M1, M2 relative to one another leads to a change of the relative arrangement of the poles of the permanent magnets M1, M2 to one another, which, in turn, effects a change of the magnetic attractions between the permanent magnets M1, M2, as a result of which a change of the distance d of the permanent magnets M1, M2 takes place, wherein the clamp 1 in a first relative rotational position of the permanent magnets M1, M2 to one another assumes a resting state, and in a second relative rotational position of the permanent magnets M1, M2 to one another assumes a working state. In other words, a clamp according to this embodiment is such that it can accommodate a fluid-carrying channel,
that it can compress an accommodated fluid-carrying channel (L) in a resting state
and that in a working state it can accommodate a fluid-carrying channel so that it is not compressed,
wherein the clamp (1) has a first permanent magnet (M1) and a second permanent magnet (M2),
wherein the magnets M1, M2 are arranged so as to be moveable relative to one another so that the magnets (M1, M2) can be rotated at least by an angle relative to one another, and that the magnets (M1, M2) can be moved linearly relative to one another, so that the distance between the magnets can vary,
wherein a rotation of the magnets (M1, M2) relative to one another leads to a change of the relative arrangement of the poles of the magnets to one another, which, in turn, effects a change of the magnetic attractions between the magnets as a result of which a change of the distance (d) of the magnets takes place, wherein the clamp in a first relative rotational position of the magnets to one another assumes a resting state, and in a second relative rotational position of the magnets to one another assumes a working state.

A fluid-carrying channel L may be, for example, a tubing line or a channel created in a cassette and delineated by a flexible wall.

This will now be explained in greater detail with reference to FIGS. 1-5, which show an example of a specific embodiment of the clamp 1 according to the invention, but not all of the elements are visible or illustrated.

Figure 3:
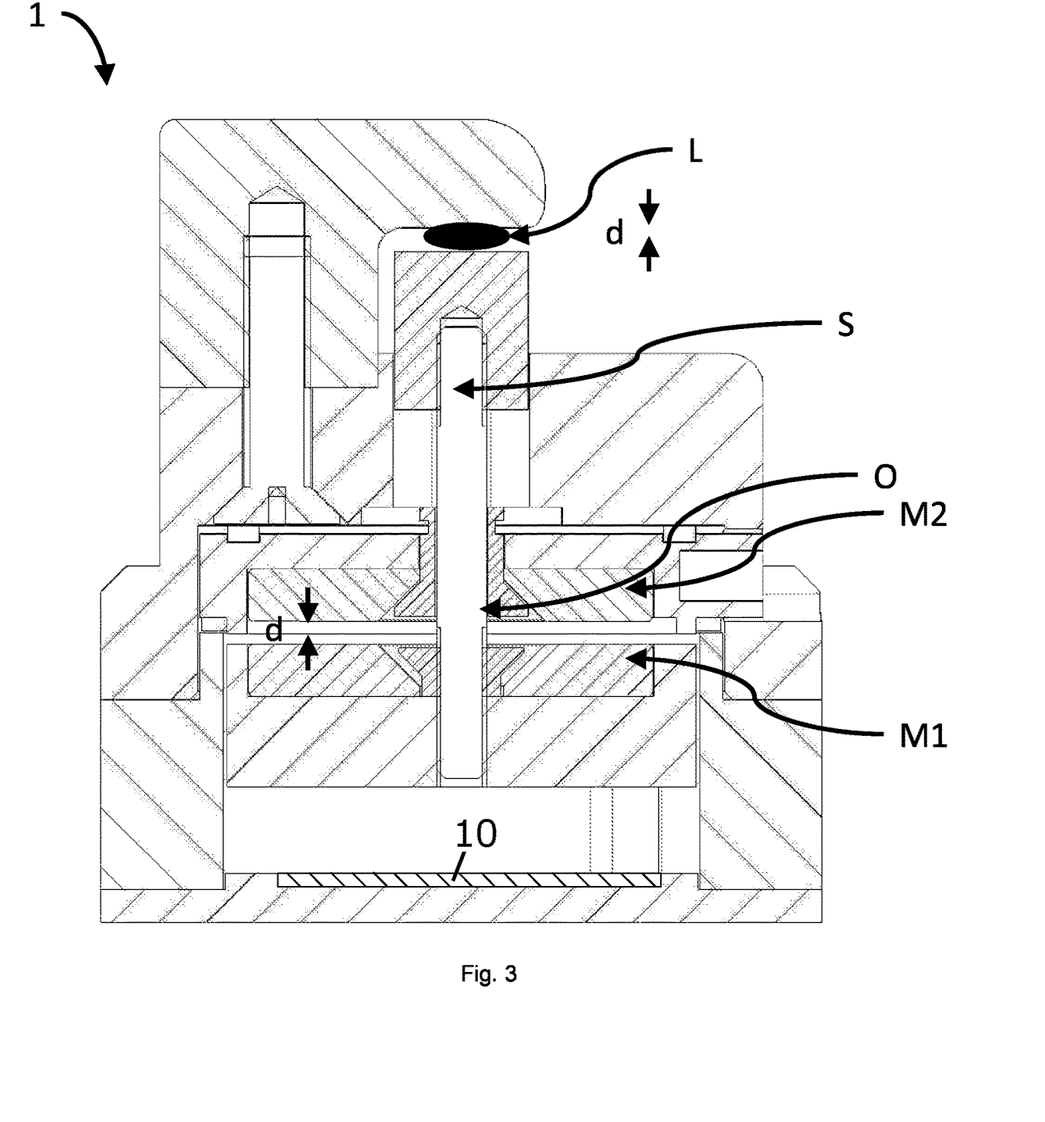
FIG. 3 shows an example of a sectional diagram of elements of a clamp according to the invention in a first condition.
Figure 4:
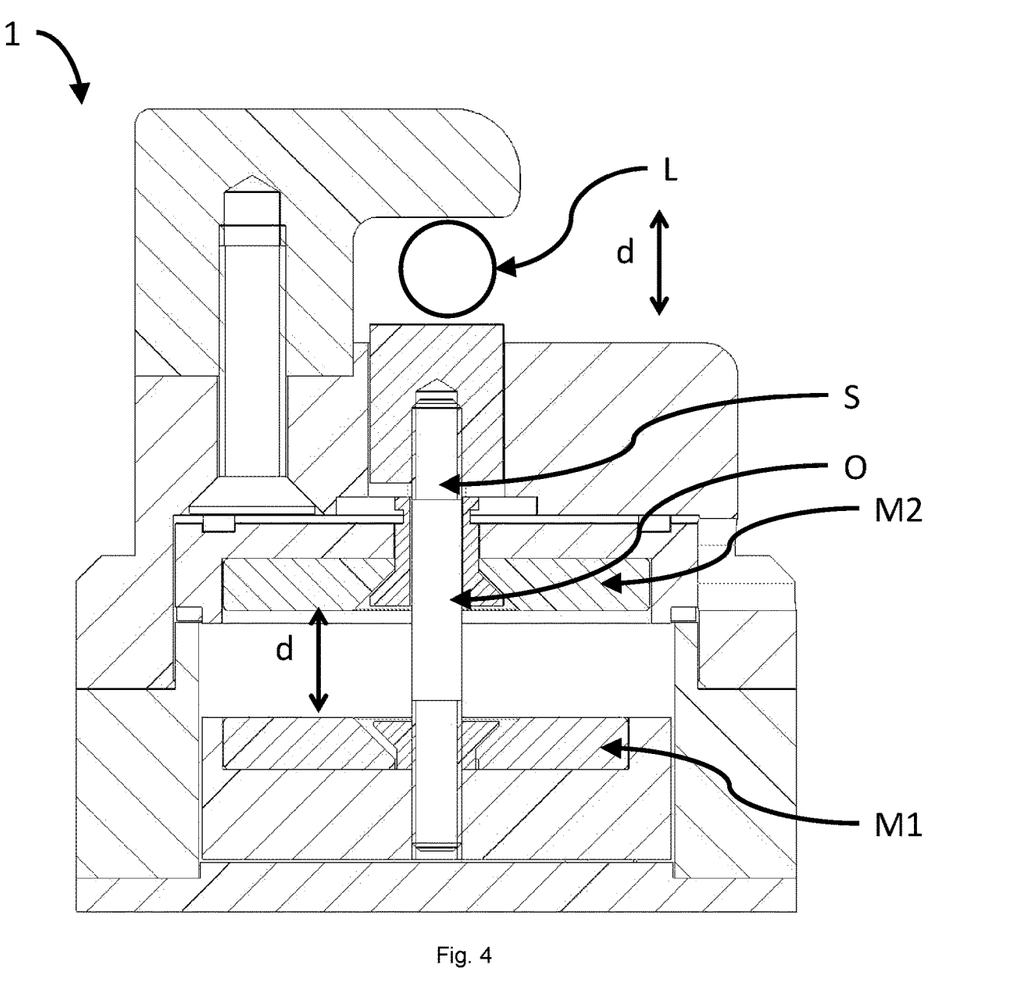
FIG. 4 shows an example of a sectional diagram of elements of a clamp according to the invention in a second condition.
Figure 5:
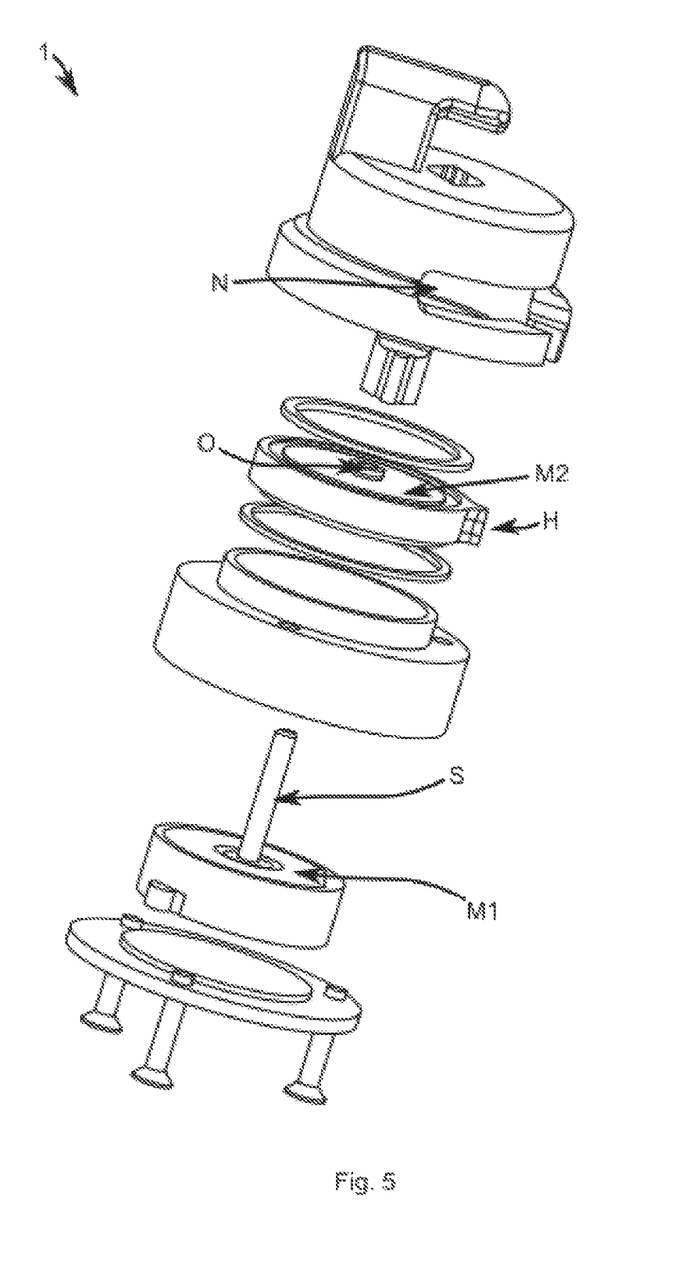
FIG. 5 shows an example of an exploded diagram of elements of a clamp according to the invention.

FIG. 3 and FIG. 4 show a clamp 1 according to the invention in a sectional view. The corresponding exploded diagram is shown in FIG. 5. FIG. 3 illustrates one embodiment having polymagnetized permanent magnets.

Polymagnetized permanent magnets can be acquired in various embodiments. Polymagnetized magnets have a plurality (even number) of sectors of different magnetization (north/south). In other words, a sector with a magnetic South pole S is next to a sector with a magnetic North pole N. Such polymagnetized magnets are available from the company Correlated Magnetics Research LLC, Huntsville, Ala. 35806 USA, for example.

As is known in general, opposite magnetic poles attract, while identical magnetic poles repel.

In the application of the invention, for example, two disk-shaped permanent magnets M1, M2 are installed, each disk having at least one South pole S and one North pole N. In the example in FIGS. 1 and 2, the permanent magnets M1 and M2 each have two South poles and one North pole.

Figure 1:
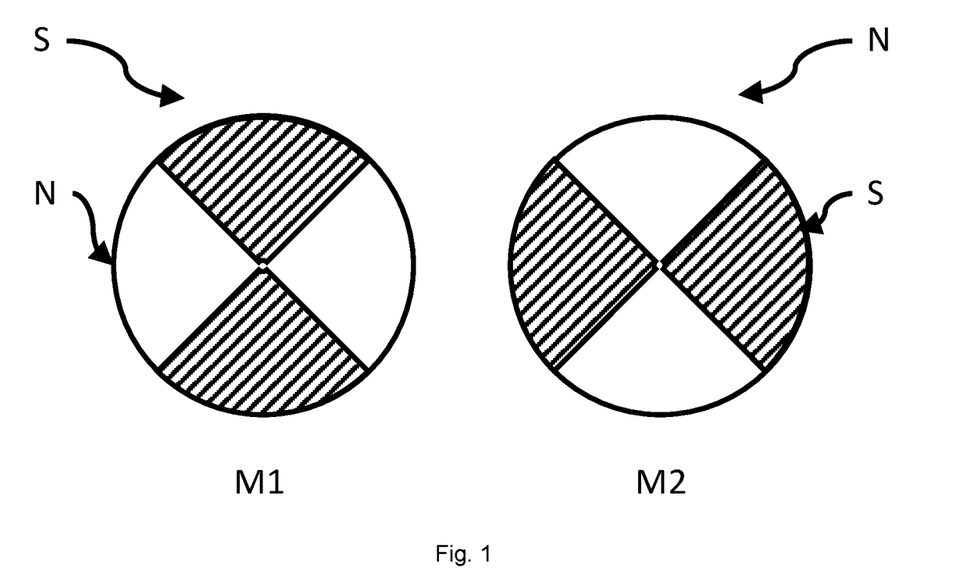
FIG. 1 shows an example of an orientation of polymagnetized permanent magnets in a first condition according to specific embodiments of the invention.

If the permanent magnet M1 is situated exactly above the permanent magnet M2, as shown in FIG. 1, then the respective poles attract, and the permanent magnets M1, M2 tend to reduce the distance d between them.

Figure 2:
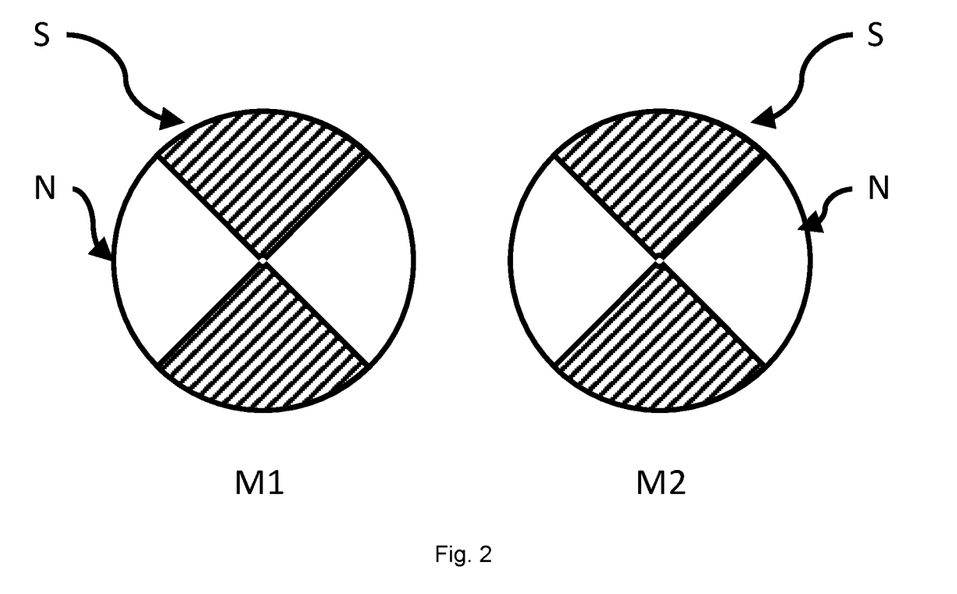
FIG. 2 shows an example of an orientation of polymagnetized permanent magnets in a second condition according to specific embodiments of the invention.

However, if the permanent magnet M1 shown in FIG. 1 is arranged exactly above the permanent magnet M2 shown in FIG. 2 then the respective poles repel one another and the permanent magnets M1, M2 tend to increase the distanced between them.

If the permanent magnets M1 and M2 are arranged between these extremes of FIG. 1 and FIG. 2, then either the repulsion effect or the attraction effect is predominant and/or the effects at one point based on the arrangement.

Although rotationally symmetrical permanent magnets M1, M2 are illustrated in FIGS. 1-5, the invention is not limited to these.

A forced path can be predetermined by means of suitable restraint and guidance.

FIG. 3 shows a resting state in which the distance is small due to the attraction of the permanent magnets M1, M2, and the inserted fluid-carrying channel L is compressed so that the flow is suppressed. An electromagnet 10 is provided and can be activated to attract permanent magnet M1 toward electromagnet 10 and away from permanent magnet M2.

In FIG. 4 however the permanent magnets M1, M2 have been rotated with respect to the resting state and the distance d is increased by guidance on a forced path. Since the force between the two permanent magnets M1, M2 decreases with an increase in rotation to the working state, the required force for maintaining such a separate state also declines.

In the embodiment illustrated here, for example, the permanent magnet M1 is held in a groove so that it can execute only a translational movement in the vertical direction. The permanent magnet M2 is also held in a groove N so that it can only execute a rotational movement such that the axis of rotation of the second permanent magnet M2 coincides with the vertical direction of the translational movement of the first permanent magnet M1. This predetermines a forced path as an example.

The figures show one embodiment in which the spring element is provided by a pair of permanent magnets (preferably polymagnetized). The permanent magnets M1, M2 are mounted or guided in such a way that one of the permanent magnets—permanent magnet M1 here—can execute a movement in z direction and at least one of the permanent magnets—permanent magnet M2 here—can execute a rotational movement. Other movement components/forced paths do not allow the bearing/guidance of the permanent magnets M1, M2. In other words, in the embodiment shown here the first permanent magnet M1 can execute a movement in z direction but cannot execute a rotational movement, while the second permanent magnet M2 can execute a rotational movement but cannot execute a movement in z direction.

In an alternative embodiment, the first permanent magnet M1 is mounted/guided in such a way that it can execute a rotational movement and a movement in z direction. The second permanent magnet M2 in this embodiment can be secured in such a way that neither a rotational movement nor a movement in z direction is possible.

Both embodiments have in common the fact that the movement of the permanent magnets M1, M2 relative to one another has both a z component and a rotational component.

It should be pointed out that such a forced path need not necessarily be designed to be "linear." Instead, the forced path may have any suitable form to provide holding forces.

In particular the forced path may also be designed, so that not only are the working state and the resting state embodied to implement an adjustable valve function but also one or more intermediate states are made possible.

Without any restriction on generality, the fluid in the fluid-carrying channel L may be a fluid such as dialysate, (arterial or venous) blood or a gas.

The figures show one embodiment with a rod-type shape, in which the rod-type shape S in the vertical direction (with respect to the diagram) is activated by the magnet M1 that is movable in the vertical direction. The rod-type shape S is passed through an opening O through the second magnet M2. The rod-type shape S can transfer the closing force to a clamping blade, for example, i.e., the mutual (attractive) forces of the first magnet M1 and of the second magnet M2 are converted into a closing force. The closing force is no longer made available by a spring (subject to fatigue). The force characteristic of the pair of magnets formed by the first magnet M1 and the second magnet M2, in which the attractive force is great to maximal at a small to minimal distance between the magnets, is converted into a force characteristic of the closing force, which is great to maximal when the clamp is closed. This effect is based on the transfer of the closing force by means of the rod.

An arrangement was described above, in which the fluid-carrying channel L is not situated between the magnets is described above, but instead a rod-type shape S is forced by the magnet M1 in the direction of a stop and thereby compresses the fluid-carrying channel L inserted between them, but this is not the only possible embodiment. Instead, the fluid-carrying channel may also be arranged between the magnets M1, M2. It should also be pointed out that the association of the resting state as well as the working state may also be chosen to be different, so that the resting state releases the fluid-carrying channel L and the working state interrupts the fluid flow in the fluid-carrying channel L, i.e., the invention is not limited to a certain form but instead may be used in any application.

In one embodiment of the invention, the first magnet M1 and/or the second magnet M2 is a polymagnetized magnet, such that a polymagnetized magnet has a first number $n_N$ of sectors with a first magnetization N and a second number $n_S$ of sectors with a second magnetization S. As a rule, the number of sectors is the same, i.e., $n=n_S=n_N$. In one embodiment, the magnetization pattern is characterized by the polymagnetized magnet method (www.polymagnet.com).

The angle range is usually logically situated between the two extreme positions (as in FIG. 1 and FIG. 2). However, it may also be appropriate to design the range to be smaller. As a rule the angle range of rotation, i.e., the difference in amount between the first angle $\alpha_{Max}$ and the second angle $\alpha_{Min}$ is smaller than or equal to 360° divided by the number of sectors n, i.e., $$\delta \le \frac{|\alpha_{Max} - \alpha_{Min}|}{n}.$$

In the embodiment in FIG. 5, a lever H is again provided for mechanical opening of the clamp 1, so that a fluid-carrying channel L can be inserted into the clamp 1. The lever H may be arranged on one of the magnets M1, M2 and/or the holder thereof. In the example in FIG. 5, the lever H is integrally molded on the holder of the magnet M2 and moves in a groove N, i.e., the lever H has the function of guidance on the forced path.

The clamp can also be opened in a currentless state and a fluid-carrying channel L can be inserted or removed.

An electromagnet which can now readily be supplied may be arranged at a suitable location in or on the clamp 1. In the case of activation, this electromagnet acts on at least one of the magnets M1, M2 in such a way that the working state is maintained, i.e., the activated electromagnet counteracts the attractive force and keeps the fluid-carrying channel L open.

The electromagnet may also be of such dimensions that it acts to open the clamp for at least one switching period in the case of activation by acting on at least one of the two magnets M1, M2 so that the working state is achieved. After achieving the working state, the current can be reduced by the electromagnet because now the forces to be applied may be lower. For example, the fact of reaching a certain position of an element of the clamp 1 may be used for current reduction by means of microswitches and/or the current is reduced after a certain period of time has elapsed. It is obviously also possible to monitor whether a certain position has been reached after a certain period of time has elapsed. If the position is not reached, a malfunction may be assumed and this can be signaled, for example.

As already described above, the forced path may have various embodiments. However, it is particularly simple for the forced path to be characterized in that the relative path of the first magnet M1 may be imaged on a helical path with respect to the second magnet M2 in the transition from the resting state to the working state.

The attractive force of the two magnets M1, M2 relative to one another makes available a closing force of the clamp 1 in the exemplary arrangement. The applied magnetization pattern causes the remaining degree of freedom of movement of the magnets M1, M2 relative to one another to have a helical component.

The magnet M1, for which a movement in z direction is possible is connected to the clamping element, which enables clamping of the fluid-carrying channel L. The magnet M2 for which the rotational movement is possible can be connected to the holding element.

Both degrees of freedom of movement when combined result in a relative helical movement. Because of the helical nature of the relationship between the z component and the movement of the clamping element and the angular movement of the magnet M2 and/or the holding element that can be connected to it, the result is that the holding forces on the holding element are much lower in the open position than the clamping forces in the closed position.

FIG. 6 shows the force-distance diagram for a traditional clamp stressed with a mechanical spring (solid line) and a clamp 1 according to embodiments of the invention (broken line). At a distance of s=0 mm, the clamp 1 releases the fluid-carrying channel L. With the traditional clamp a spring is thereby held by a holding element under tension in this position. If the holding element releases the spring, the spring relaxes until the fluid-carrying channel is completely closed (at s=6 mm here), wherein the residual tension in the spring ensures an adequate closure in the closed position. In the embodiment with polymagnetized magnets M1, M2, a comparable closing force is achieved in the closed position, on the one hand, while a definitely smaller force must be applied by the holding element for the holding force in the open position, on the other hand. In other words, since lower forces are now necessary to keep the fluid-carrying channel L open, the energy consumption by the clamp 1 is also reduced in comparison with traditional clamps.

The fluid-carrying channel L can be used by manual opening of the clamp 1 with a lever connected to the holding element. Due to the low holding forces, the electromagnet may be designed with small dimensions and may be lighter as well as requiring a lower holding current, which is associated with a lower energy consumption.

If the holding current is turned off, the two magnets follow an attraction movement relative to one another along the helical path of movement on the clamping element goes into the closed position.

This embodiment is suitable in particular with clamps 1 for fluid-carrying channels L, by means of which medical fluids such as blood or infusion fluids can be directed into or away from a patient. Then the clamp 1 may be embodied as a part of a blood treatment machine, a peritoneal dialysis machine or an infusion pump, for example. If a defect situation occurs in such machines, in particular in the event of an interruption in the electrical power supply to the machine or the clamp 1, it is necessary to induce a safe state, in which the fluid connection to the patient is interrupted. A holding element, which is designed as an electromagnet and switches from the resting state to the working state by means of power uptake by activation, would necessarily switch from the working state to the resting state in the event of a power failure and would thus interrupt the flow through the fluid-carrying channel L, and the safe state would be achieved.

In further embodiments, a clamp 1 according to the invention has friction-reducing elements, such as, for example, one or a plurality of slide bushes O. Such a slide bush O could be arranged, for example, around a pusher-like molding S, e.g. around a pin or plunger S, which is guided through this bush O and the movement of which is associated with a rotation of the two permanent magnets M1, M2 relative to one another and a change of the distance of the permanent magnets to one another. Material combinations are thereby particularly advantageous between slide bush O and pusher/pin/plunger S supported therein, which have a static friction, which is as low as possible when at rest, i.e. which do not have a so-called stick-slip effect, thus have a breakaway torque, which is as small as possible. One example for such a material combination is, for example, a pusher/pin/plunger S, which is arranged in a slide bush O made of plastic. In this combination, plastics with admixtures of PTFE, graphite or boron nitrite are particularly advantageous. Steels can in particular be stainless steels. Ceramic and silicon carbide are furthermore possible as materials for slide bushes O. Such a slide bush O advantageously provides for a more low-friction movement of a pusher/pin/plunger S supported therein, which can be connected directly to a locking element/clamp element of the clamp 1. Quicker closing times, less wear, and a longer service life of such a clamp 1 are made possible thereby in a particularly advantageous manner.

In a further development, a clamp 1 according to the invention has, instead of a slide bush O, one or a plurality of slide elements, which are arranged around a movable part. It can be particularly advantageous thereby to not arrange slide elements around the entire circumference e.g. of a movable pusher/pin/plunger S, but only in circle segments, which, as a whole, cover less than 360 degrees. The need for sliding element material can thereby be lowered in a particularly advantageous manner, in that parts of a circumference are piecewise equipped with sliding elements around part, which can slide therein.

Particularly preferably, the permanent magnets M1, M2 of the clamp 1 are arranged in a housing of a non-magnetic material, such as, for example, aluminum or plastic.

Aspects of the invention can be combined as follows: By means of the pair of permanent magnets M1, M2, which can be moved relative to one another, an additional linear movement—e.g. normal to the rotation plane—is triggered by means of a rotational movement. Due to the magnetic coupling of the permanent magnets M1, M2 to one another, a relative rotational movement leads to a relative lifting movement, i.e. the linear distance between the permanent magnets M1, M2 changes as a result of a relative rotational movement.

This process is reversible. A relative rotational movement in a first direction of rotation leads to a reduction of the distance of the permanent magnets M1, M2, and a relative rotational movement in a second (opposite) direction of rotation leads to an increase of the distance.

According to the invention, the conversion of a rotational movement into an additional lifting movement can be attained in that the permanent magnets M1, M2 are designed, are movably supported and are arranged so that, in a first rotational position, the sum of the attraction between the permanent magnets M1, M2 is smaller than for a second rotational position. This can be attained, for example, in that the distances of attracting poles on average is greater in the first rotational position than in the second rotational position, However, this can take place instead or in addition via the number, the shape, and the design of the poles. Much less electrical energy has to be expended for such a relative rotational movement and for a holding of a certain rotational position than had been the case with known clamps, in order to keep a clamp in the open position.

The invention claimed is:

1. A clamp comprising:
    a clamp element;
    a first permanent magnet having a central axis of rotation, a first central opening surrounding the central axis of rotation, a North pole sector of magnetization, a South pole sector of magnetization arranged radially adjacent the North pole sector of magnetization, and a top surface;
    a second permanent magnet having a second central axis of rotation, a second central opening surrounding the second central axis of rotation, a second North pole sector of magnetization, a second South pole sector of magnetization arranged radially adjacent the second North pole sector of magnetization, and a bottom surface; and
    a guide rod secured in the first central opening and configured for movement with the first permanent magnet, the guide rod passing through the second central opening, configured for movement through the second permanent magnet, and configured for transferring a closing force to the clamp element, wherein
    the top surface of the first permanent magnet faces the bottom surface of the second permanent magnet,
    the clamp element is configured to accommodate a fluid-carrying duct,
        the clamp element is configured to compress the fluid-carrying duct, in a resting state,
        the clamp element is configured, in a working state, to accommodate the fluid carrying duct so that the fluid-carrying duct is not compressed,
        the first permanent magnet and the second permanent magnet are arranged at a distance from one another,
        the first and second permanent magnets are configured to be rotated about an angle relative to one another whereby the rotation of the first and second permanent magnets relative to one another results in either a reduction in the distance from one another or an increase in the distance from one another,
        the resting state results from relative rotation to a first angle, and the working state results from relative rotation to a second angle.

2. The clamp according to claim 1, wherein the fluid-carrying duct is accommodated in the clamp element, a fluid is in the fluid-carrying duct, and the fluid is a liquid.

3. The clamp according to claim 1, wherein the first permanent magnet and/or the second permanent magnet is a polymagnetized magnet, wherein the polymagnetized magnet has a plurality of sectors of a first magnetization and a plurality of sectors of a second magnetization.

4. The clamp according to claim 3, wherein a difference in degrees between the first and the second angle is less than or equal to 360° divided by a sum of the two pluralities of sectors.

5. The clamp according to claim 1, wherein the clamp further comprises a lever configured to open the clamp to accommodate the fluid-carrying duct.

6. The clamp according to claim 1, wherein the clamp further comprises an electromagnet configured to act on at least one of the permanent magnets such that, in the event of activation, the working state is maintained.

7. The clamp according to claim 1, wherein an electromagnet acts on at least one of the permanent magnets such that, in the event of activation, the working state is achieved.

8. The clamp according to claim 1, wherein the first permanent magnet is guided on a helical path relative to the second permanent magnet in transitioning from the resting state to the working state.

9. The clamp according to claim 1, wherein the first permanent magnet is disk-shaped.

10. The clamp according to claim 1, wherein the second permanent magnet is disk-shaped.

11. The clamp according to claim 1, wherein the first permanent magnet is disk-shaped and the second permanent magnet is disk-shaped.

12. The clamp according to claim 1, wherein the first permanent magnet and the second permanent magnet are rotationally symmetrical with respect to each other.

13. A clamp comprising:
a clamp element;
a first permanent magnet having a central axis of rotation; and
a second permanent magnet having a second central axis of rotation, wherein
the clamp element is configured to accommodate a fluid-carrying duct,
the clamp element is configured to compress the fluid-carrying duct, in a resting state,
the clamp element is configured to accommodate the fluid-carrying duct in a working state, such that the fluid-carrying duct is not compressed,
the resting state results from relative rotation of the first permanent magnet to a first angle with respect to the second permanent magnet,
the working state results from relative rotation of the first permanent magnet to a second angle with respect to the second permanent magnet, and
the fluid-carrying duct is arranged between the first and second permanent magnets.

* * * * *